(12) United States Patent
Kessler et al.

(10) Patent No.: US 7,090,720 B2
(45) Date of Patent: Aug. 15, 2006

(54) USE OF BIOACTIVE GLASS IN DENTAL FILLING MATERIAL

(75) Inventors: Susanne Kessler, Ergolding (DE); Sean Lee, Karlsruhe (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 10/471,148

(22) PCT Filed: Mar. 8, 2002

(86) PCT No.: PCT/DE02/00827

§ 371 (c)(1),
(2), (4) Date: Nov. 3, 2003

(87) PCT Pub. No.: WO02/072038

PCT Pub. Date: Sep. 19, 2002

(65) Prior Publication Data

US 2004/0065228 A1 Apr. 8, 2004

(30) Foreign Application Priority Data

Mar. 9, 2001 (DE) ................................. 101 11 449

(51) Int. Cl.
  *A61K 6/06* (2006.01)
  *A61K 6/083* (2006.01)
(52) U.S. Cl. ................. 106/35; 523/116; 523/117; 523/115; 433/226; 433/228.1
(58) Field of Classification Search .................. 106/35; 433/226, 228.1; 501/63, 70; 523/116, 117, 523/115

See application file for complete search history.

(56) References Cited

U.S. PATENT DOCUMENTS

| | | | |
|---|---|---|---|
| 3,862,920 A * | 1/1975 | Foster et al. ................. | 523/116 |
| 3,926,906 A * | 12/1975 | Lee et al. ..................... | 523/116 |
| 3,932,938 A * | 1/1976 | Mackta ..................... | 433/228.1 |
| 5,055,497 A * | 10/1991 | Okada et al. ............... | 523/116 |
| 5,074,916 A | 12/1991 | Hench et al. | |
| 5,340,776 A | 8/1994 | Paschke et al. | |
| 5,527,836 A * | 6/1996 | Yamamuro et al. ......... | 523/116 |
| 5,735,942 A * | 4/1998 | Litkowski et al. ............ | 106/35 |
| 5,810,595 A * | 9/1998 | Mallow ................... | 433/228.1 |
| 5,891,233 A | 4/1999 | Salonen et al. | |
| 6,086,374 A * | 7/2000 | Litkowski et al. ........ | 433/217.1 |
| 6,136,885 A * | 10/2000 | Rusin et al. ................. | 523/116 |
| 6,297,181 B1 * | 10/2001 | Kunert et al. ................. | 501/57 |
| 6,353,038 B1 * | 3/2002 | Aho et al. ................... | 523/105 |
| 6,787,584 B1 * | 9/2004 | Jia et al. ..................... | 523/115 |
| 2003/0113686 A1 * | 6/2003 | Jia et al. ..................... | 433/81 |
| 2003/0167967 A1 * | 9/2003 | Narhi et al. .................. | 106/35 |

FOREIGN PATENT DOCUMENTS

| | | |
|---|---|---|
| DE | 25 01 683 | 7/1976 |
| DE | 41 00 604 C | 2/1992 |
| DE | 690 12 260 T2 | 1/1995 |
| DE | 198 58 126 A | 6/1999 |
| DE | 198 14 133 A1 | 10/1999 |
| EP | 0 634 373 A | 1/1995 |
| EP | 0 716 049 A | 6/1996 |
| EP | 0 997 132 A | 5/2000 |
| WO | 96/21628 | 7/1996 |
| WO | 97 27148 A | 7/1997 |
| WO | WO 97/271148 * | 7/1997 |
| WO | 99/07326 | 2/1999 |

OTHER PUBLICATIONS

U.S. Appl. No. 60/336,500.*
John Rectenwald, et al: "Bioglass Elicits an Anti-Inflammatory Response in Mouse . . . ", Department of Surgery, University of Florida College of Medicine, Gainesville, Florida, May 11, 1999, pp. 1-21.
Larry L. Hench & June Wilson "An Introduction to Bioceramics", Advanced Series in Ceramics, vol. 1, World Scientific, 1993, pp. 41-63.
Larry L. Hench and Jon K. West: "Biological Applications of Bioactive Glasses", Life Chemistry Reports, 1996, vol. 13, pp. 187-241.
Allan, et al: "The Antibacterial Properties of a Bioactive Glass", Department of Microbiology and Periodontology, Eastman Debtal Institute, London.
Rectenwald et al: "Bioglass Elicits and Anti-Inflammatory . . . ", Surgical Infection Society, 19-th Annual Meeting, Apr.-May 1999, p. 1.
Chemical Abstracts 133-63889, 2001.
Chemical Abstracts 133:242 711, 2001.
Chemical Abstracts 131:23 437, 2001.
Introduction to Dental Material, Richard Von Boort, Mosely Editorial, UK, 1991, pp. 90-147.
Ullman's Encyclopedia of Industrial Chemistry, 6th Electronic Edition, 1998, pp. 1-11.

\* cited by examiner

*Primary Examiner*—C. Melissa Koslow
(74) *Attorney, Agent, or Firm*—Michael J. Striker

(57) ABSTRACT

The dental filling material for a permanent dental filling contains up to 87 percent by weight of a mixture of bioactive glass particles capable of forming a hydroxylapatite layer and conventional non-bioactive dental glass particles surrounded or embedded in a matrix material. The glass particles have an average particle size ($d_{50}$) less than 50 μm. When the index of refraction of the glass particles at least approximately matches the index of refraction of the matrix material a particularly attractive appearance results when the resulting filling material is used to make a dental filling. When the bioactive glass particles contain fluoride, protection against further caries is provided. The invention also includes a method of making the dental filling material, the dental filling made with it and a binder for binding the dental filling to a tooth.

21 Claims, No Drawings

USE OF BIOACTIVE GLASS IN DENTAL FILLING MATERIAL

BACKGROUND OF THE INVENTION

The invention relates to the production of aesthetic, permanent dental filling material that does not discolor and that counteracts the occurrence of secondary caries.

In tooth restorations, for aesthetic reasons, the goal is for the restored tooth region to be as effectively invisible as possible, so that it is visually indistinguishable from the natural tooth. Thus far, this has been done with composites, compomers and glass-ionomer cements, or with expensive porcelain or glass ceramic inlays, with variable results. However, such fillings have only inadequate durability and are quickly washed out. They also tend to discolor.

Bioactive glasses have already been known for long time and are described in summary fashion for instance by Larry L. Hench and John K. West in "Biological Applications of Bioactive Glasses", Life Chemistry Reports 1996, Vol. 13, pages 187–241, or in "An Introduction to Bioceramics", L. Hench and J. Wilson, Eds., World Scientific, New Jersey (1993). In contrast to conventional glasses, bioactive glasses are distinguished by being soluble in an aqueous medium and by forming a film of hydroxyl apatite on their surface. The most commonly used bioactive glasses are produced either as fusible glass, which then have a markedly lower proportion of $SiO_2$ compared to normal window or bottle glasses, and a substantially higher proportion of sodium, or else are so-called sol-gel glasses, which in contrast to fusible glasses can contain a high proportion silicon oxide and a slight to completely absent amount of sodium.

The essential properties of bioactive glass are known to one skilled in the art and are described for instance in U.S. Pat. No. 5,074,916. According to this reference, bioactive glass differs from conventional lime-sodium-silicate glasses in that it binds living tissue.

Such bioactive glasses are used for instance for healing bone damage, and in particular as synthetic bone transplant material. They are moreover successfully used for healing chronic wounds, especially with diabetic ulcers and in pressure sores and bedsores in geriatrics. For instance, John E. Rectenwald, Sean Lee and Lyle L. Moldawer et al. (Infection and Immunity, submitted for publication) have been able to demonstrate that in the mouse, bioactive glass displays an inflammatory effect which by stimulation of interleukin-6 (IL-6) activity with simultaneous inhibition of the inflammation-stimulating cytokines TNF-alpha, IL-1-alpha and IL-10, as well as MPO (myeloperoxidase) (see also 19th Annual Meeting, Surgical Infection Society 1999, Apr. 28 to May 1, 1999).

From E. Allen, et al. (Departments of Microbiology in Periodontology, Eastman Dental Institute), it is also known that a bioactive glass 45-S-5, which can be procured from Bioglas® U.S. Biomaterials, Alachua, Fla. 32615, USA and which has an antibacterial action. Such an action cannot be achieved with normal glass beads (window glass).

SUMMARY OF THE INVENTION

In International Patent Disclosure WO 97/27148, it is proposed that bioactive glass of a defined composition be used for remineralization of teeth. The bioactive glass comprises powder with two different particle sizes, namely those with an average particle size of at most 90 μm and those of at most 10 μm. For remineralization, the bioactive glass releases minerals that are dentally important by means of ion exchange, and the large particles are intended to serve as an ion reservoir. By this means, new apatite, in particular hydroxyl apatite, is developed which cannot be distinguished from the natural hydroxyl apatite of the tooth. The bioactive glass moreover has a desensitizing and an antibacterial action at the same time. The small particles are intended to penetrate fine dental defects, such as fissures, and close them and coat them. Particularly with multiple applications, dental defects are intended to be sealed in this way.

From U.S. Pat. No. 5,891,233, the use of a material containing bioactive glass as an underlining for a temporary dental filling is known. In this reference, the bioactive glass has the task of remineralizing tiny canals in the dentin and preventing tooth irritation and pain. The use of a material primarily comprising bioactive glass is also proposed as a temporary filling of the root canal in order to stabilize it before it is later replaced with a final filling. In this reference as well, it has already been proposed that prostheses crowned with this material be temporarily stabilized before being finally crowned.

In German Patent Disclosure DE 198 14 133, self-disinfecting plastics for the dental field are described that have reduced adhesion of microorganisms and contain biocidal substances which kill off the microorganisms within 24 hours. As biocidal substances, silver, copper and zinc as well as organic compounds, such as ciprofloxalin, chlorhexidine, and others, are described.

In International Patent Disclosure WO 99/07326, a cement composition with an antimicrobial effect is described that is intended for use in the medical field (bone cement, implant components) and the dental field (filling materials, adhesives, sealing media, and restorative material). It is intended to overcome the disadvantages that occur from the release of fluoride ions from glass-ionomer cements in the prior art. The fluoride is intended to attain an antimicrobial effect. The release of fluoride from the glass matrix and its replacement with other ions in fact causes a structural change in both the cement and the cavity, an effect that is to be avoided. Moreover, the release exhausts the fluoride content in the matrix material, so that this material must typically be regenerated if a continuous effect against harmful bacteria is to be achieved. For this reason, for attaining an antimicrobial effect, it is proposed that the dental filling material have an antimicrobially active zeolite added to it. However, the reference also says that such zeolites cause discoloration of the polymer material, causing them not to be colorfast. The zeolite used is intended to release biocidal metal ions, such as silver ions, over time.

Long-term use of bioactive glass has not been described until now, since it was assumed that it would partly dissolve and become porous from contact with bodily fluid, releasing Ca, Na and P. The material has therefore been used thus far only as a temporary dental filling material.

The object of the invention is to furnish a dental filling material which remains not just temporarily but permanently in the tooth, is essentially invisible, and does not become discolored over time. Moreover, it should not have the disadvantages of the prior art, and in particular it should prevent the development of secondary caries. Finally, it should also have high mechanical load-bearing capacity and hardness, eliminate sensitivity to pain, and have an antimicrobial action. According to the invention, these objects are attained by the characteristics defined in the claims.

It has in fact been discovered surprisingly that by a combination of bioactive glass and conventional dental glass, mixtures can be produced that when bound in a matrix are invisible and indistinguishable from the natural tooth material. According to the invention, the procedure is such that first the index of refraction of the matrix material is determined, and then a conventional dental glass is selected or mixed in that has the same or virtually the same index of refraction as the matrix. The term "virtually the same index of refraction" is understood to mean all indexes of refraction that are no longer visually apparent. It has been demonstrated that the index of refraction of bioactive glass is negligible if the indexes of refraction of dental glass and the matrix are essentially the same. This pertains particularly to the quantitative proportions preferred. Such mixtures or kits that contain the components in appropriate proportions can easily be prefabricated by the manufacturer, so that the dentist need merely mix the components together.

In this way, it is possible to furnish dental filling materials with an extremely aesthetic effect, particularly for the visible range, that are mechanically strong and hard and that furthermore do not become discolored over time. Moreover, such filling materials have excellent properties for avoiding pain and for protecting the healthy tooth material.

Since bioactive glass is in fact soluble, it was to be expected that on contact with water-containing bodily fluids such as saliva, or beverages, it would dissolve to the extent that it is either in gel form or becomes so porous that it fractures at the tiniest stress. By incorporating a bioactive glass into the dental filling material, it was therefore to be expected that after the partial dissolution or solubilizing, what would be left behind would be new cavities and a hollow network in the dental filling that impairs the strength of the filling.

Moreover, modern dental fillings are typically secured in the drilled-out cavity using plastic adhesives. For these plastic adhesives to hold sufficiently, the natural dentin in the cavity must first be etched with an acid, to create a rougher surface to which the actual adhesive material adheres better. To that end, phosphoric acid and an organic acid such as methacrylic acid are preferably used. In modern dental filling techniques, however, this is done in a single step; that is, adhesive materials or so-called bondings are used which already contain the appropriate acids mixed in with them and thus etch the tooth material during the bonding process. Since bioactive glasses have an extraordinarily high pH value, it is to be expected that dental filling materials that contain these glasses will neutralize the bonding immediately, or shift the pH value of the bonding so far that it becomes alkaline, thus hindering the etching effect. As a result, it is to be expected that the adhesive effect, that is, the adhesive force, is reduced. This is not so problematic in temporary fillings, but for use as a permanent filling, such adhesive sites must be anchored especially durably in the tooth material.

It has now surprisingly been discovered that the cavities caused by solubilizing of the glass material do not impair the overall internal durability of the filling, or if so, only negligibly. Even the adhesive strength of the bondings, which is enhanced by etching with acids, is surprisingly not reduced by the highly alkaline bioglasses.

Pronounced solubilizing of the bioactive glass particles occurs only at the surface of the filling. It has now also been discovered that this phenomenon is so slight that it is no greater or only insignificantly or in other words negligibly greater than the simultaneously occurring natural abrasion of the tooth and the filling material, which amounts to approximately 10 μm per year. The course over time of this solubility is controlled by the diffusion of the Ca, Na and phosphate ions out of the glass.

In the interior of the filling, the diffusion of moisture through the matrix and the diffusion of the Ca and Na ions through the matrix also occur, as a speed-determining step.

In the dental glasses of low solubility that have been used until now, individual glass particles located at the surface are completely dissolved out over time, creating open pores in the filling surface where microorganisms can colonize; these pores also provide additional surface area that can be attacked by mechanically abrasive degradation.

It has now been discovered that in bioactive glass, the above mechanism does not occur; instead, because of the low hardness, a different mechanism is involved. Specifically, if such a glass particle is released at the surface of the filling, it is partly dissolved by the saliva and then releases Na, Ca and P ions, with which the teeth and in particular the tooth material surrounding the filling become remineralized. Thus the bioactive glass acts as both a durable anticaries agent and as a durable desensitizing agent in teeth that are pain-sensitive to heat, cold, acid and sweetness. Because of the permanent release of remineralizing and hence tooth-protecting ions, a comparatively soft silica gel film as well as a hydroxyl apatite film, which is slowly worn down by chewing motions, are created at the surface of the glass particle. In the process, the glass is removed to approximately the same extent as the resin matrix of the filling. The open pores at the surface of the filling known from the conventional dental glasses are accordingly not created.

According to the invention, it is therefore proposed that material containing bioactive glass also be used as a permanent dental filling.

As a result, the favorable properties of the bioactive glass material can also be utilized for permanent dental fillings, particularly its capability of forming apatite and a desensitizing tooth irritation, as well as its permanently bacteriostatic and in particular cariostatic effects.

The bacteriostatic effect and remineralization at the chewing surface, and in the initial period after the placement of the filling, come into play at the peripheral gaps that may occur from polymerization shrinkage (if bonding is inadequate), but also come into play directly at the surface of the cavity.

The bioactive glasses contained according to the invention are preferably a conventional bioactive glass which is quite well known to one skilled in the art. Such glasses typically contain a maximum of 60 weight-% $SiO_2$, a high proportion of $Na_2O$ and CaO, as well as phosphorus, specifically in a high molar ratio of calcium to phosphorus, which usually but not necessarily ranges around approximately 5.

If such bioactive glasses come into contact with water or a bodily fluid, they are distinguished by special reactions; specifically, sodium and calcium ions of the glass are replaced with $H^+$ ions out of the solution, in a cation exchange reaction, creating a surface that has silanol groups onto which sodium hydroxide and calcium hydroxide are deposited. The enhancement of the hydroxy ion concentration at the surface of the glass then causes a further reaction with the silicon network, creating further silanol groups that can also be located at greater depths in the glass.

Because of the highly alkaline pH in the glass interstice, a mixed hydroxyl apatite phase comprising CaO and $P_2O_5$ occurs, which crystallizes out at the $SiO_2$ surface and in biological materials bonds with mucopolysaccharides, collagens, and glycoproteins.

The molar ratio of calcium to phosphorus is preferably <2 and in particular <3 and preferably >30, in particular >20; ratios of <10 are especially preferred.

Tooth filling materials that contain bioactive glass particles which have $SiO_2$, $CaO$, $Na_2O$, $P_2O_5$, $CaF_2$, $B_2O_3$, $K_2O$, and/or $MgO$ are especially preferred. If the dental filling material contains bioactive glass particles of fusible glass, then they preferably have, in terms of the total weight of glass, from 35 to 60 and preferably 35 to 55 weight-% of $SiO_2$; 10 to 35, and preferably 15 to 35 weight-% of CaO; 10 to 35, and preferably 15 to 35, weight-% of $Na_2O$; 1 to 12, and preferably 2 to 8, weight-% of $P_2O_5$; 0 to 25 weight-% of $CaF_2$; 0 to 10 weight-% of $B_2O_3$; 0 to 8 weight-% of $K_2O$; and/or 0 to 5 weight-% of MgO. If the bioactive glass is a fusible glass, then the upper limit of silicon dioxide contained is approximately 60 and preferably 55 weight-%; an upper limit of 50 weight-% is especially preferred. The sodium oxide content is preferably more than 15 weight-%, in particular more than 18 weight-%. A sodium oxide content of <20 weight-% is especially preferred.

If the bioactive glass contained in the dental filling material of the invention is a bioactive glass that is produced by sol-gel methods, then its proportion of silicon dioxide can be markedly higher than in fusible glasses, and its proportion of sodium oxide can be equal to 0. Bioactive glasses produced by a sol-gel method preferably contain from 40 to 90 weight-% of $SiO_2$, 4 to 45 weight-% of CaO, 0 to 10 weight-% of $Na_2O$, 2 to 16 weight-% of $P_2O_5$, 0 to 25 weight-% of $CaF_2$, 0 to 4 weight-% of $B_2O_3$, 0 to 8 weight-% of $K_2O$, and/or 0 to 5 weight-% of MgO.

In both types of bioactive glasses described above, the phosphorous oxide content is preferably at least 2 weight-% and in particular at least 4 weight-%.

The glass particles are contained in the dental fillings of the invention with an average particle size of $d_{50}<50$ μm, in particular <20 μm or <10 μm; particle sizes of <5 μm are particularly preferred. In principle, a higher ratio of surface area to weight or volume brings about a higher sterilizing biocidal action than with larger particles. A particularly pronounced biocidal action of the bioactive glass is attained for instance with particles of average sizes of $d_{50}<2$ and in particular <1 μm. The particle sizes $d_{50}$ and $d_{99}$ indicate the equivalent diameter at which the total distribution of particles assumes the value of 50% and 99%, respectively. The particles for the glass particles used, that is, both for the conventional dental glasses and for the bioglasses, are preferably the same or are in the same range. The particle size distribution is such that the value $d_{99}$ amounts to at maximum ten times and preferably at maximum eight times and in particular seven times the $d_{50}$ value. Particle distributions with a $d_{99}$ value that at maximum amounts to about five times the $d_{50}$ value are preferred. The $d_{99}$ values that are usual for the use according to the invention are a maximum of 100 μm, preferably a maximum 50 μm, and in particular a maximum of 30 μm. In special cases, the particle sizes for the $d_{99}$ value are a maximum of 20 μm. Particles with low grinding abrasion are very particularly preferred.

Typical indexes of refraction $n_d$ for dental glasses amount according to the invention to from 1.45 to 1.9, and preferably 1.49 to 1.8. The upper limits of the dental glasses used according to the invention are typically 1.9, preferably 1.8, and in particular at maximum 1.65; the lower limits are approximately 1.45, and in particular 1.48 and typically 1.49. The classical range for such glasses is approximately 1.50 to 1.60, and in particular 1.56. Conventional dental glasses are widely known and are commercially available for instance from Schott Glas in Landshut, Germany.

If the proportion of bioglass is less than 20 weight-%, in particular less than 10 weight-%, referred to the total content of glass particles, then it has been demonstrated that it is possible to ignore its index of refraction, and a dental glass can be used whose index of refraction is the same or virtually the same as that of the matrix, or in other words is visually undistinguishable or negligible.

By silanization, the glass particles used according to the invention can be better bonded, in particular into a plastic matrix, resulting in higher mechanical loading values, such as bending strength and compressive strength, and a higher Vickers hardness. Typical silanizing agents are known to one skilled in the art; purely as an example, 3-methacryloyloxypropyl trimethoxysilane can be named.

The total proportion of the glasses in the dental filling material is typically at most 87% or 85%; a maximum of 80% and in particular a maximum of 70% is preferred. In some cases, maximum values of 70% and in particular 65% have proved sufficient. According to the invention, the proportion of bioactive glass in the total glass is at maximum 50%, and a maximum of 40% and in particular a maximum of 20 weight-% is preferred.

The dental glass used according to the invention can be either an inert or a reactive dental glass. Inert dental glasses are those that release ions not at all, or only insignificantly. In other words, they themselves are not reactive. Inert dental glasses of this kind are usually alkali-free glasses. Non-inert or in other words reactive dental glasses are those which can release ions and which react with the matrix, in particular the plastic monomer, or contribute themselves to the curing of the matrix. These include the usual compomer glasses and glass-ionomer cement glasses. In general, compomer glasses and glass-ionomer cements are the same or comparable. However, compomer glasses are bound in a matrix in which they are less reactive, and thus they have a substantially longer curing time. They are therefore typically used along with light-curing monomers or a light-activated starter. According to the invention, however, they are preferred over reactive matrixes. Inert dental glasses are quite particularly preferred. The dental filling material produced according to the invention is preferably free of zeolites.

The proportion of bioactive glass in the matrix material is preferably at most 40 and expediently up to 20 vol.-%, preferably up to 15 vol.-% and in particular at most 10 vol.-%, with 2 to 10 vol.-% and in particular 4 to 6, or 5, vol.-% being especially preferred.

In the dental filling material of the invention, the bioactive glass is typically bound in a plastic resin matrix that additionally contains nonbioactive, conventional dental glass particles. Preferably, the bioactive glass and/or the nonbioactive dental glass components are silanized, to enable better bonding of the glass with the plastic resin matrix. Such silanizations and plastic resin matrixes are known to one skilled in the art (see for example Introduction to Dental Materials by Richard von Noort, published by Mosely in the UK) and are described for instance in appropriate dental textbooks, or in Ullmann's Encyclopedia of Industrial Chemistry, 4$^{th}$ electronic edition, Dental Materials. The dental filling material of the invention, which contains bioactive glass, is then obtained. It should be pointed out briefly at this point that hereinafter—as is generally conventional—the composition of the individual glass is given in weight-%. The composition of composite materials or of the dental filling matrix, however, is given in vol.-%—as is usual in the dental field.

As the binder in the dental filling matrix, PMMA (polymethyl methacrylate) and bis-GMA, which is a polymer of bisphenol A, di(2,3-epoxypropyl) ether (so-called bomb monomer) and acrylic acid, are used.

In a very special embodiment, the matrix, but in particular the bioactive glass contained in it, contains barium and/or strontium, in order to render the filling radiopaque; optionally, it also includes zinc. To that end, the calcium in the bioactive glass is replaced partially by zinc, barium and/or strontium, which is already possible in the production of the basic glass composition, or for instance by ion exchange. In general, a radiopaque medium can also be added separately to the finished glass powder and/or to the other ingredients in the dental filling material.

In a preferred exemplary embodiment of a dental filling material containing bioactive glass, a glass-plastic composite is proposed, using bioactive glass and optionally a conventional dental glass. Practical dental plastics predominantly include UV-curable resin based on acrylate, methacrylate, 2,2-bis-[4-(3-methacryloxy-2-hydroxypropoxy)phenyl]propane(bis-GMA)urethane methacrylate, alkanediol dimethacrylate, or cyanacrylate.

If the material that contains bioactive glass according to the invention is used in glass-ionomer cement, then it can additionally contain typical organic acids used in dental materials, such as acrylic acid, itaconic acid, maleic acid, tartaric acid, and optionally a conventional glass-ionomer glass.

Preferably, the optical index of refraction of the bioactive glass is approximately the same as the index of refraction of the matrix material surrounding the glass. As a result, all the filling material becomes clearly transparent and is then practically undistinguishable from the natural tooth enamel, which is especially advantageous if the teeth have been bleached white for cosmetic reasons. The index of refraction of the filling preferably amounts to from 1.45 to 1.65, and particularly 1.5 to 1.6.

According to the invention, a mixture of bioactive glass with normal dental glass is used. They can be used in an arbitrary mixture ratio. The proportion or in other words filling degree of glass in such composite materials is at maximum 90 vol.-% and preferably at least 10 vol.-%, particularly at least 15 vol.-% and especially preferably at least 30 vol.-%; from 65 to 85 vol.-% and from 70 to 80 vol.-% are quite particularly preferred. Of this, the proportion of bioactive glass, that is, the proportion in the total glass, amounts preferably to up to 40 and in particular up to 20 vol.-%; 3 to 10 and preferably 4 to 6 vol.-% are especially preferred.

In an embodiment according to the invention, one or more opacifiers and/or one or more pigments, such as $TiO_2$, are added to the filling material. It is thus possible to adapt the color of the filling to the natural color of the actual tooth.

The particulate bioactive glass preferably has an average particle size $d_{50}$ of <10 μm, expediently <5 μm, preferably <4 μm, and especially preferably 0.5 to 2 μm. As a result, the surface of the permanent dental filling can be optimally polished without causing roughness. A method for grinding glass to such a particle size is described in German Patent DE 41 00 604 C1, corresponding to U.S. Pat. No. 5,340,776.

The glass particles are preferably contained in pastelike material, a solution, or a suspension. Such pastes and so forth can be obtained for instance by suspending the glass particles in a solvent. Preferred solvents are water, acetone, ethers, esters, and mixtures and emulsions thereof. Especially preferably, the solvents at least partly include highly volatile solvents. Expediently, further bioactive substances and materials, such as mineral salts, organic reaction components, preservatives, and biocidal and especially bactericidal agents are added to the solvents. An especially preferred solvent is a normal saline solution.

The bioactive glass material can optionally contain still other oxides or salts of one or more of the elements Na, K, Ca, Mg, B, Ti, P, F, or still other elements and substances, in various proportions.

The bioactive glass material can also be used according to the invention directly in binding agents (bonding) for bonding a dental filling to a tooth, more or less as a viscous substance. The invention thus also pertains to bonding that contains bioactive material. This boundary area between filling and tooth is vulnerable to secondary caries, especially from the development of gaps after polymerization shrinkage of the filling. The antibacterial and anticariotic action of bioactive glass now comes into play. This aspect has significance on its own.

To prevent caries, the bioactive glass can contain fluorine. To that end, one of the raw materials for the melt for instance is added proportionally as fluoride, expediently in the form of a salt. The fluoride then typically is added in an amount of up to 20 weight-%, expediently up to 10%, in the glass; 2 to 10 weight-% is especially preferred. In many cases, a fluoride content of up to 5% or 0.1 to 5 weight-% and even up to 2% or 1 to 2 weight-% (in each case referred to the fluoride ion) has proved adequate. However, it is also possible to add fluoride to the filling material, specifically separately and/or in the form of a premixture, for instance with the resin or plastic. The weight-%s employed are then the same as in the glass.

The invention claimed is:

1. A dental filling material for an aesthetic permanent dental filling, said dental filling material containing a resin matrix and up to 87 percent by weight of glass particles, wherein said glass particles have an average particle size ($d_{50}$) less than 50 μm, said glass particles comprise bioactive glass particles and non-bioactive dental glass particles, said bioactive glass particles are capable of forming a hydroxylapatite layer and comprise a bioactive glass material in which calcium is replaced in part with strontium and/or barium.

2. The dental filling material as defined in claim 1, wherein said resin matrix contains at most 20 percent by volume of said bioactive glass particles.

3. The dental filing material as defined in claim 1, wherein said resin matrix contains from 2 to 40 percent by volume of said bioactive glass particles.

4. The dental filling material as defined in claim 1, wherein said resin matrix has an index of refraction approximately equal to an index of refraction of said bioactive glass particles and/or an index of refraction of said non-bioactive dental glass particles.

5. The dental filling material as defined in claim 1, wherein said non-bioactive dental glass particles have an index of refraction of from 1.48 to 1.65.

6. The dental filling material as defined in claim 1, wherein said bioactive glass particles and/or said non-bioactive dental glass particles are silanized for binding into the resin matrix.

7. The dental filling material as defined in claim 1, further comprising opacifiers and/or colored pigments.

8. The dental filling material as defined in claim 7, wherein said opacifiers comprise $TiO_2$.

9. The dental filling material as defined in claim 1, wherein said bioactive glass particles and said non-bioactive dental glass particles are embedded in said resin matrix, and wherein at least one of said resin matrix, said bioactive glass particles and said non-bioactive dental glass particles contain a radioopaque substance.

10. The dental filling material as defined in claim 1, wherein said resin matrix comprises an acrylate binder.

11. The dental filling material as defined in claim 10, wherein said acrylate binder is polymethyl methacrylate and/or bis-GMA.

12. The dental filling material as defined in claim 1, wherein said average particle size ($d_{50}$) is less than 5 μm.

13. The dental filling material as defined in claim 1, wherein said average particle size ($d_{50}$) is less than 4 μm.

14. The dental filling material as defined in claim 1, wherein said average particle size ($d_{50}$) is less than 2 μm.

15. A permanent dental filling made from the dental filling material as defined in claim 1.

16. A dental filling material for an aesthetic permanent dental filling, said dental filling material containing up to 87 percent by weight of glass particles, wherein said glass particles have an average particle size ($d_{50}$) less than 50 μm and said glass particles comprise bioactive glass particles and non-bioactive dental glass particles, wherein said bioactive glass particles are capable of forming a hydroxylapatite layer, wherein said bioactive glass particles contain from 2 to 10 percent by weight fluoride.

17. A dental filling comprising a dental filling material and a binder for binding the dental filling material to a tooth, wherein said binder contains bioactive glass particles and said dental filling material contains a resin matrix and up to 87 percent by weight of glass particles, wherein said glass particles have an average particle size ($d_{50}$) less than 50 μm and said glass particles comprise said bioactive glass particles and non-bioactive dental glass particles, wherein said bioactive glass particles are capable of fanning a hydroxylapatite layer and said resin matrix includes up to 40% by volume of said bioactive glass particles.

18. A composite-reinforced glass-ionomer cement for dental applications, said cement containing bioactive glass, wherein said bioactive glass is capable of forming a hydroxylapatite layer.

19. A method of making a dental filling material for an aesthetic permanent dental filing, said method comprising the steps of:
   a) providing a matrix material for the dental filling material and ascertaining an index of refraction of the matrix material;
   b) providing non-bioactive dental glass particles consisting of a non-bioactive dental glass having an index of refraction approximately equal to the index of refraction of the matrix material;
   c) mixing bioactive glass particles and said non-bioactive dental glass particles in the matrix material to form the dental filling material with up to 87 percent by weight of said glass particles;
   wherein the glass particles have an average particle size ($d_{50}$) less than 50 μm, said bioactive glass particles are capable of forming a hydroxylapatite layer and said bioactive class particles comprise a bioactive class material in which calcium is replaced in part with strontium and/or barium.

20. The method as defined in claim 19, further comprising silanizing said bioactive glass particles and said non-bioactive dental glass particles prior to said mixing.

21. The method as defined in claim 19, wherein the matrix material contains up to 40 percent by volume of said bioactive glass particles.

* * * * *